United States Patent [19]

Minderhoud et al.

[11] Patent Number: 4,522,939
[45] Date of Patent: Jun. 11, 1985

[54] PREPARATION OF CATALYST FOR PRODUCING MIDDLE DISTILLATES FROM SYNGAS

[75] Inventors: Johannes K. Minderhoud; Martin F. M. Post, both of Amsterdam, Netherlands

[73] Assignee: Shell Oil Company, Houston, Tex.

[21] Appl. No.: 594,618

[22] Filed: Mar. 29, 1984

[30] Foreign Application Priority Data

May 31, 1983 [NL] Netherlands ............ 8301922

[51] Int. Cl.³ ............ B01J 21/04; B01J 21/06; B01J 21/08; B01J 23/86
[52] U.S. Cl. .................. 502/242; 502/256; 502/314; 502/332; 518/714; 518/715
[58] Field of Search ........... 502/242, 256, 314, 332; 518/714, 715

[56] References Cited

U.S. PATENT DOCUMENTS 4,385,193  5/1983  Bijwaard et al. ............ 502/242 X
4,410,637 10/1983  Kortbeek et al. ............ 518/715 X Primary Examiner—W. J. Shine

[57] ABSTRACT

A process for preparing a catalyst for converting syngas to middle distillates which comprises kneading and/or impregnating cobalt and another metal (Zr, Ti, Cr) onto a carrier ($SiO_2$, $Al_2O_3$, $SiO_2/Al_2O_3$) in such a way that L and S satisfy the relation:

$$(3+4R) > (L/S) > (0.3+0.4R), \text{ wherein}$$

L = the total quantity of cobalt present on the catalyst, expressed as mg Co/ml catalyst;
S = the surface area of the catalyst, expressed as $M^2$/ml catalyst; and R = the weight ratio of the quantity of cobalt deposited on the catalyst by kneading to the total quantity of cobalt present on the catalyst.

17 Claims, No Drawings

PREPARATION OF CATALYST FOR PRODUCING MIDDLE DISTILLATES FROM SYNGAS

BACKGROUND OF THE INVENTION

The invention relates to a process for the preparation of a catalyst suitable for the conversion of a mixture of carbon monoxide and hydrogen into hydrocarbons, particularly middle distillates.

The preparation of hydrocarbons from a $H_2/CO$ mixture by contacting this mixture at elevated temperature and pressure with a catalyst is known in the literature as the Fischer-Tropsch hydrocarbon synthesis. Catalyst often used for the purpose comprise one or more metals from the iron group, together with one or more promotors, and a carrier material. These catalysts can suitably be prepared by known techniques, such as precipitation, impregnation, kneading and melting. The products which can be prepared by using these catalysts usually have a very wide range of molecular weight distributions and, in addition to branched and unbranched paraffins, often contain considerable amounts of olefins and oxygen-containing organic compounds. Usually only a minor portion of the products obtained is made up of middle distillates. Of these middle distillates not only the yield but also the pour point is unsatisfactory. Therefore the direct conversion of $H_2/CO$ mixtures according to Fischer-Tropsch is not a very attractive route for the production of middle distillates on a technical scale.

In this patent application "middle distillates" should be taken to be hydrocarbon mixtures whose boiling range corresponds substantially with that of the kerosene and gas oil fractions obtained in the conventional atmospheric distillation of crude mineral oil. During said distillation, from the crude mineral oil are separated in succession: one or more gasoline fractions having a boiling range between 30° C. and 200° C., one or more kerosene fractions having a boiling range between 140° and 300° C. and one or more gas oil fractions having a boiling range between 180° and 370° C.

Recently a class of Fischer-Tropsch catalysts was found which have the property of yielding a product in which only very few olefins and oxygen-containing compounds occur and which consists virtually completely of unbranched paraffins, a considerable portion of which paraffins boils above the middle distillate range. It has been found that by using a catalytic hydrotreatment this product can be converted in high yield into middle distillates. As feed for the hydrotreatment at least the part of the product is chosen whose initial boiling point lies above the final boiling point of the heaviest middle distillate desired as end product. The hydrotreatment, which is characterized by a very low hydrogen consumption, leads to middle distillates with a considerably better pour point than those obtained in the direct conversion of a $H_2/CO$ mixture according to Fischer-Tropsch.

The Fischer-Tropsch catalysts belonging to the above-mentioned class contain silica, alumina or silica-alumina as carrier material and cobalt together with zirconium, titanium and/or chromium as catalytically active metals, in such quantities that the catalysts comprise 3-60 pbw cobalt and 0.1-100 pbw of at least one other metal chosen from zirconium, titanium or chromium per 100 pbw carrier material. The catalysts are prepared by depositing the metals involved on the carrier material by kneading and/or impregnation.

The catalyst preparation by impregnation is carried out by contacting a porous carrier with a compound of the relevant metal in the presence of a liquid, followed by removal of the liquid. Likewise, in the catalyst preparation by kneading a porous carrier is contacted with a compound of the relevant metal in the presence of a liquid, followed by removal of the liquid, the distinction being that preceding and/or during the removal of the liquid the composition is subjected to intensive mechanical treatment, such as pressing, kneading or wringing, which as a rule leads to a considerable reduction of the particle size of the carrier material and to the composition taking on the consistency of a paste. Usually several hours' kneading in a suitable kneading machine is sufficient to attain the desired homogeneity of distribution of the components over the mixture. The intensive mechanical treatment during which there is a considerable reduction of the particle size of the carrier material is the main difference between the kneading route and the impregnation route. It is true that during the preparation of a catalyst by impregnation there may be a stage at which the composition contains an amount of liquid corresponding to that present in the paste mentioned hereinbefore and that some mechanical energy may be supplied to the composition, for instance by stirring, but on the whole the particle size of the carrier material will remain virtually unchanged during the catalyst preparation by impregnation.

In the case of the present catalysts which in addition to cobalt comprise another metal, the term "catalyst preparation by kneading and/or impregnation" as used herein includes every possible variant in which the two metals have been deposited on the carrier in this way. For instance, the cobalt may be deposited on the carrier entirely by kneading and the other metal entirely be impregnation, but it is also possible to deposit part of the cobalt and/or the other metal by impregnation, while the rest is deposited by kneading; Likewise, there is a free choice as to the order in which the metals are deposited on the carrier and the number of steps used to carry out the catalyst preparation.

SUMMARY OF THE INVENTION

Further investigation into the preparation and the performance of the above-mentioned cobalt catalysts has now revealed that where activity and stability are concerned, their performance depends to a great extent on three factors, viz.

(a) the total quantity of cobalt present on the catalyst, (b) the weight ratio of the quantity of cobalt deposited on the catalyst by kneading to the total quantity of cobalt present on the catalyst, and (c) the surface area of the catalyst.

It has been found that the catalysts show optimum performance as to activity and stability when they satisfy the relation $$(3+4R) > (L/S) > (0.3+0.4R),$$

wherein

L = the total quantity of cobalt present on the catalyst, expressed as mg Co/ml catalyst;

S = the surface area of the catalyst, expressed as $m^2$/ml catalyst; and

R = the weight ratio of the quantity of cobalt deposited on the catalyst by kneading to the total quantity of cobalt present on the catalyst.

Since R can vary between 0 (for a catalyst onto which the cobalt has been deposited exclusively by impregnation) and 1 (for a catalyst onto which the cobalt has been deposited exclusively by kneading), the present invention only relates to catalysts having a quotient of L by S higher than 0.3 but lower than 7. Depending on the manner in which the cobalt has been deposited, the above-mentioned relation can be used to indicate—within the range 0.3-7—the area wherewithin the quotient of L by S should lie in order to ensure optimum catalyst performance. We believe the catalysts whose quotients of L by S satisfy the above-mentioned relation to be novel.

The present patent application therefore relates to a process for the preparation of a catalyst in which a catalyst is prepared by kneading and/or impregnation, which catalyst comprises 3-60 pbw cobalt and 0.1-100 pbw of at least one other metal chosen from zirconium, titanium or chromium per 100 pbw silica, alumina or silica-alumina and whose L and S are such as to satisfy the relation $$(3+4R) > (L/S) > (0.3+0.4R).$$

DETAILED DESCRIPTION OF THE INVENTION

On the basis of the value of R the catalysts which can be prepared according to the invention may be divided into three main classes, viz.

(I) catalysts wherein R=0,
(II) catalysts wherein R=1, and
(III) catalysts wherein 1>R>0.

The catalysts belonging to class I may further be divided into two subclasses, viz.

(IA) catalysts in the preparation of which impregnation has been used exclusively, and
(IB) catalysts in the preparation of which both impregnation and kneading have been used, but in which the cobalt has been deposited exclusively by impregnation.

The catalysts belonging to class II may also be further divided into two subclasses, viz.

(IIA) catalysts in the preparation of which kneading has been used exclusively, and
(IIB) catalysts in the preparation of which both impregnation and kneading have been used, but in which the cobalt has been deposited exclusively by kneading.

The catalysts belonging to class III are characterized in that the cobalt has been deposited partly by impregnation and partly by kneading.

Each of the above-mentioned classes offers a wide range of possibilities of variation, depending, among other things, on the number of steps used to carry out the preparation, on the order in which the metals are deposited and on whether during the treating steps the metals are deposited together or individually.

In order to give an impression of the possibilities of variation within a certain class, a schematic enumeration of a number of methods of preparing the catalysts belonging to class IA is given hereinafter. Since in the preparation of the catalysts belonging to this class, as in the preparation of the catalysts belonging to class IIA, there is only one way of depositing the metals (exclusively by impregnation in class IA and exclusively by kneading in class IIA), the possibilities of variation of these two classes are relatively few in comparison with the other classes. The enumeration has been restricted to methods of preparation in which at most three impregnation steps are carried out. For the sake of simplicity in the schematic representation impregnation with a cobalt compound is given as "Co", impregnation with a compound of another metal as "Zr", and simultaneous impregnation with a cobalt compound and a compound of another metal (what is called co-impregnation) as (Co+Zr). If one confines oneself to methods of preparation in which exclusively separate impregnations or exclusively co-impregnation are used, the following possibilities offer:

one step: (Co+Zr)
two steps: Co/Zr; Zr/Co; (Co+Zr)/(Co+Zr)
three steps: Co/Co/Zr; Co/Zr/Zr; Zr/Co/Co; Zr/Zr/Co; Co/Zr/Co; Zr/Co/Zr; (Co+Zr)/(Co+Zr)/(Co+Zr).

If in addition there is taken into account the possibility of the preparation being carried out by a combination of separate impregnation with co-impregnation, then the number of possibilities of variation will be much bigger yet. For instance, in the two-step process the following embodiments may also be considered: Co/(Co+Zr); Zr/(Co+Zr); (Co+Zr)/Co; (Co+Zr)/Zr.

Both when the metal is deposited by impregnation and when the metal is deposited by kneading the carrier material is first contacted with a compound of the relevant metal in the presence of a liquid. As metal compounds both organic and inorganic compounds are eligible. Mixtures of metal compounds may also be used. The liquid used may be organic or inorganic. Mixtures of liquids may also be used. Both during impregnation and during kneading it is preferred to contact the carrier material with a solution of the relevant metal compound in a solvent. For the deposition of cobalt preference is given to the use of a solution of an inorganic cobalt solution in water. For the deposition of the other metal it is preferred to use a solution of an organic metal compound in an organic solvent or mixture of organic solvents. It is preferred that the organic solvent consist at least partly of a $\beta$-diketone or a $\beta$-keto-ester. Especially preferred are solvents containing more than 0.5 gram molecule of a $\beta$-diketone or a $\beta$-keto-ester per gram atom of the other metal. If a certain metal is deposited in more than one step, the various steps can be carried out using different compounds of the metal involved and different solvents. The amounts of liquid used during impregnation may vary within wide limits. The quantity of liquid used may be equal to, or smaller or larger than, the pore volume of the carrier to be impregnated. It is preferred in the impregnation to use a quantity of liquid the volume of which corresponds substantially to the pore volume of the carrier to be impregnated. The quantities of liquid used during kneading may also vary within wide ranges; however, care should be taken that during kneading so much liquid is present that, together with the carrier material and the metal compound, under the action of the intensive mechanical treatment it can produce a composition having the desired paste-like consistency. A surplus of liquid, if any, can be removed from the composition before or during kneading by evaporation. It is preferred during the kneading to use a quantity of liquid the volume of which corresponds to 110-190% of the pore volume of the carrier.

In the catalyst preparation according to the invention the liquid present in the composition is preferably removed after each step in which a metal compound has been deposited on the carrier material, for instance at an elevated temperature, before the composition is once more contacted with a metal compound in a following step. After the last step of deposition a metal compound on the carrier the composition is calcined. It is preferred in the catalyst preparation according to the invention to calcine the composition obtained after each treatment step.

As stated hereinbefore, the present invention comprises a large number of variant preparation methods which differ from one another chiefly in the manners in which the metals are deposited on the carrier material (exclusively by kneading, exclusively by impregnation or by a combination thereof), the number of steps in which the preparation is carried out and the order in which the metals are deposited. The catalysts are preferably prepared by one of the three procedures following:

(a) first cobalt is deposited in one or more steps by impregnation, and subsequently the other metal is deposited in one or more steps, also by impregnation;

(b) first the other metal is deposited in one or more steps by impregnation, and subsequently cobalt is deposited in one or more steps, also by impregnation; and (c) first cobalt is deposited in one or more steps by kneading and subsequently the other metal is deposited in one or more steps by impregnation.

The quantities of metal deposited on the catalysts according to the invention are 3–60 pbw per 100 pbw carrier for cobalt, and 0.1–100 pbw per 100 pbw carrier for the other metal. It is preferred to prepare catalysts containing 15–50 pbw cobalt per 100 pbw carrier. The preferred quantity to be deposited of the other metal is dependent on the way in which this metal is deposited. In the modes of preparation in which first the cobalt is deposited on the carrier and then the way in which this metal is deposited on the carrier and then the other metal, preference is given to the preparation of catalysts containing 0.1–5 pbw of the other metal per 100 pbw carrier. In the modes of preparation in which first the other metal is deposited on the carrier and then the cobalt, preference is given to the preparation of catalysts containing 5–40 pbw of the other metal per 100 pbw carrier. Preference is given to the use of zirconium as other metal and silica as carrier material.

The catalysts prepared according to the process of the invention are excellently suitable for use in the preparation of hydrocarbons from a mixture of carbon monoxide and hydrogen. The present patent application therefore also relates to a process for the preparation of hydrocarbons from a $H_2$-and-CO-containing feed by using a catalyst which has been prepared according to the invention. Before they are suitable to be used for this purpose the catalysts must first be reduced. This reduction may very suitably be carried out by contacting the catalyst at a temperature between 200° and 350° C. with a hydrogen-containing gas. The conversion of the $H_2$-and-CO-containing feed into hydrocarbons is preferably carried out at a temperature 25°–135° C. and in particular of 175°–275° C. and a pressure of 5–150 bar and in particular of 10–100 bar.

$H_2$-and-CO-containing feeds which are eligible to be converted into hydrocarbons by using a catalyst prepared according to the invention may very suitably be obtained from a heavy carbonaceous material, such as coal, by gasification, or from light hydrocarbons, such as natural gas, by steam reforming or partial oxidation. Suitable $H_2$-and-CO-containing feeds may also be obtained by separating a fraction containing unconverted hydrogen and carbon monoxide and other components, if desired, from the reaction product obtained by contacting a $H_2/CO$ mixture with a catalyst containing one or more metal components having catalytic activity for the conversion of a $H_2/CO$ mixture into hydrocarbons and/or oxygen-containing organic compounds. In this partial conversion of the $H_2/CO$ mixture, depending on the catalyst chosen therefor, there will be produced either mainly aromatic hydrocarbons, or mainly paraffinic hydrocarbons or mainly oxygen-containing organic compounds. If in the partial conversion it is the object to produce mainly aromatic hydrocarbons, use can very suitably be made of a catalyst mixture containing either a methanol or dimethyl ether synthesis catalyst or a $Fe/Mg/Al_2O_3$ or $Fe/Cr/SiO_2$ catalyst prepared by impregnation, together with a crystalline metal silicate which is characterized in that after one hour's calcination in air at 500° C. it has the following properties:

(a) an X-ray powder diffraction pattern in which the strongest lines are the lines given in Table A,

TABLE A d(Å)
11.1±0.2
10.0±0.2
3.84±0.07
3.72±0.06; and (b) in addition to $SiO_2$, includes one or more oxides of a trivalent metal M chosen from the group formed by aluminum, iron, gallium, rhodium, chromium and scandium; and in which the $SiO_2/M_2O_3$ molar ratio is higher than 10.

If in the partial conversion it is the object to produce mainly paraffinic hydrocarbons, use can very suitably be made of the above-mentioned $Fe/Mg/Al_2O_3$ or $Fe/Cr/SiO_2$ catalysts prepared by impregnation. If the partial conversion is carried out with the object of producing oxygen-containing organic compounds, use can very suitably be made of a methanol or dimethyl ether synthesis catalyst. Methanol synthesis catalysts suitable for use in the partial conversion are $ZnO/Cr_2O_3$ and $Cu/ZnO/Cr_2O_3$ catalysts. A dimethyl ether synthesis catalyst suitable for use in the partial conversion is a mixture of gamma-$Al_2O_3$ and the $Cu/ZnO/Cr_2O_3$ methanol synthesis catalyst mentioned before.

The $H_2$-and-CO-containing feed which is converted into hydrocarbons by using a catalyst prepared according to the invention preferably has a $H_2/CO$ molar ratio higher than 1.5. If the feed has a $H_2/CO$ molar ratio lower than 1.5, the latter is preferably raised to have a value between 1.5 and 2.25 before it is contacted with the cobalt catalyst. The $H_2/CO$ molar ratio of low-hydrogen feeds may be raised, for instance, by adding hydrogen, removing carbon monoxide, mixing with a hydrogen-rich $H_2/CO$ mixture, or subjecting the low-hydrogen feed to the CO shift reaction.

As remarked hereinbefore, the catalysts prepared according to the invention when used for the conversion of a $H_2$-and-CO-containing feed yield a substantially paraffinic product whose high-boiling part can be converted in high yield into middle distillates by the use of a catalytic hydrotreatment. The feed for the hydrotreatment chosen is at least the part of the product whose initial boiling point lies above the final boiling point of the heaviest middle distillate desired as end product. The catalytic hydrotreatment is carried out by contacting the fraction to be treated at elevated temperature and pressure and in the presence of hydrogen with a catalyst containing one or more metals with hydrogenation activity supported on a carrier. Examples of suitable catalysts are sulfidic catalysts containing nickel and/or cobalt and, in addition, molybdenum and/or tungsten supported on a carrier such as alumina or silica-alumina. In the catalytic hydrotreatment it is preferred to use a catalyst containing one or more noble metals from Group VIII supported on a carrier. The quantity of noble metal present on the carrier may vary within wide limits, but often it will be 0.5–5%w. The noble metals from Group VIII which may be present on the carrier are platinum, palladium, rhodium, ruthenium, iridium and osmium, platinum being preferred. Two or more of these metals may be present in the catalysts, if desired. The quantity of the Group VIII noble metal present in the catalyst is preferably 0.1–2%w and in particular 0.1–1%w. Examples of suitable carriers for the noble metal catalysts are amorphous oxides of the elements from Groups II, III and IV, such as silica, alumina, magnesia and zirconia, as well as mixtures of these oxides, such as silica-alumina, silica-magnesia and silica-zirconia and zeolitic materials, such as mordenite and faujasite. As carriers for the noble metals catalysts aluminas and silica-aluminas are preferred. A noble metal catalyst very suitable for the present purpose is a catalyst containing one or more noble metals from Group VIII supported on a carrier, 13–15%w of which carrier consists of alumina, the remainder of silica. Suitable conditions for carrying out the catalytic hydrotreatment are a temperature of 175°–400° C., a hydrogen partial pressure of 10–250 bar, a space velocity of 0.1–5 kg.l$^{-1}$.h$^{-1}$ and a hydrogen/oil ratio of 100–5000N l.kg$^{-1}$. The catalytic hydrotreatment is preferably carried out under the following conditions: a temperature of 250°–350° C., a hydrogen partial pressure of 25–150 bar, a space velocity of 0.25–2 kg.l$^{-1}$.h$^{-1}$ and a hydrogen/oil ratio of 250–2500N l.kg$^{-1}$. A suitable choice of catalyst and treating conditions offers the possibility of producing in the catalytic hydrotreatment from a heavy fraction of the product prepared over the cobalt catalyst not only middle distillate, but also lubricating oil having a high viscosity index.

The invention is now illustrated with the aid of the following example.

Catalyst preparation

21 Co/Zr/SiO$_2$ catalysts (Catalysts 1–21) were prepared by impregnating and/or kneading silica carriers with solutions of cobalt and zirconium compounds. Furthermore there was prepared one Co/Ti/SiO$_2$ catalyst (Catalyst 22) by impregnation of a silica carrier with a solution of a cobalt compound and with a solution of a titanium compound.

In each impregnation step a quantity of solution was used the volume of which corresponded substantially with the pore volume of the carrier involved. After each impregnation step the solvent was removed by heating and the material was calcinated at 500° C.

In each kneading step a quantity of solution was used the volume of which corresponded substantially with 150% of the pore volume of the carrier involved. In each kneading step the mixture was kneaded in a macerator for three hours. During the kneading a small portion of the solvent was removed by heating. After each kneading step the paste obtained was collected from the macerator, the remainder of the solvent was removed by heating, and the material was ground and calcined at 500° C.

Catalysts 1–22 were prepared as follows.

Catalysts 1–5

Three-step impregnation of various silica carriers with a solution of zirconium tetra-n-propoxide in a mixture of n-propanol and benzene, followed by one-step impregnation of the zirconium-loaded carriers with a solution of cobalt nitrate in water.

Catalysts 6, 7 and 9

One-step impregnation of various silica carriers with a solution of cobalt nitrate, followed by one-step impregnation of the cobalt-loaded carriers with a solution of zirconium nitrate in water.

Catalyst 8

One-step co-impregnation of a silica carrier with a solution of cobalt nitrate and zirconyl chloride in water.

Catalyst 10

Two-step impregnation of a silica carrier with a solution of cobalt nitrate in water, followed by one-step impregnation of the cobalt-loaded carrier with a solution of zirconium nitrate in water.

Catalyst 11

One-step co-impregnation of a silica carrier with a solution of cobalt nitrate and zirconium nitrate in water.

Catalyst 12

One-step impregnation of a silica carrier with a solution of cobalt nitrate in water, followed by kneading of the cobalt-loaded carrier with a solution of zirconium nitrate in water.

Catalyst 13

Kneading of a silica carrier with a solution of zirconium tetra-n-propoxide in a mixture of n-propanol, acetyl acetone and benzene, followed by one-step impregnation of a zirconium-loaded carrier with a solution of cobalt nitrate in water.

Catalysts 14–17

Kneading of various silica carriers with a solution of cobalt nitrate in water, followed by one-step impregnation of the cobalt-loaded carriers with a solution of zirconyl chloride in water.

Catalyst 18

Co-kneading of a silica carrier with a solution of cobalt nitrate and zirconium nitrate in water.

Catalyst 19

Kneading of a silica carrier with a solution of cobalt nitrate in water, followed by kneading of the cobalt-loaded carrier with a solution of zirconium nitrate in water.

Catalyst 20

Kneading of a silica carrier with a solution of zirconium nitrate in water, followed by kneading of the zirconium-loaded carrier with a solution of cobalt nitrate in water.

Catalyst 21

Three-step impregnation of a silica carrier with a solution of zirconium tetra-n-propoxide in a mixture of toluene and acetyl acetone, followed by kneading of the zirconium-loaded carrier with a solution of cobalt nitrate in water.

Catalyst 22

Three-step impregnation of a silica carrier with a solution of tetraisopropyl ortho-titanate in a mixture of isopropanol and acetyl acetone, followed by one-step impregnation of the titanium-loaded carrier with a solution of cobalt nitrate in water.

Further information on Catalysts 1-22 is given in Tables I and II.

In the case of the catalysts listed in Table I the cobalt was deposited exclusively by impregnation. For these catalysts R=0, and therefore the quotient of L by S should, according to the invention, lie between 0.3 and 3. Of the catalysts listed in Table I Catalysts 2, 3, 5, 9, 11-13 and 22 are catalysts according to the invention, having L/S between 0.3 and 3. Catalysts 1, 4, 6-8 and 10, having L/S<0.3 or >3, fall outside the scope of the invention. They have been included in the patent application for comparison.

In the case of the catalysts listed in Table II the cobalt was deposited exclusively by kneading. Of these catalysts R=1 and therefore the quotient of L by S should lie between 0.7 and 7. Of the catalysts listed in Table II Catalysts 15, 16 and 18-21 are catalysts according to the invention, having L/S between 0.7 and 7. Catalysts 14 and 17, having L/S<7 or >0.7, fall outside the scope of the invention. They have been included in the patent application for comparison.

Catalyst testing

Catalysts 1-10, 14-17 and 22 were used in nineteen experiments (Experiments 1-19) in the preparation of hydrocarbons from mixtures of carbon monoxide and hydrogen. The experiments were carried out in a 50-ml reactor containing a fixed catalyst bed. Prior to the testing the catalysts were reduced in a hydrogen-containing gas at 250° C.

In Experiments 1-5 and 19 a $H_2/CO$ mixture having a $H_2/CO$ molar ratio of 2 was contacted with catalysts 1-5 and 22 at a temperature of 220° C., a pressure of 20 bar and at various space velocities. The results of these experiment are given in Table III.

Of the experiments given in Table III Experiments 2, 3, 5 and 19 are experiments according to the invention. In these experiments use was made of catalysts according to the invention which showed both a high activity (expressed as g $C_1^+$/g cobalt/h) and a high stability (expressed as %v loss of CO conversion/100 h). Experiments 1 and 4 fall outside the scope of the invention. The catalysts used in these experiments have too low stability. The catalysts used in Experiment 4 moreover had too low activity.

In Experiments 6-14 $H_2/CO$ mixtures were contacted with Catalysts 6-10 at various temperatures, pressures and space velocities. The conditions under which the experiments were carried out, as well as the results of the experiments, are given in Table IV.

Of the experiments listed in Table IV only Experiment 13 is an experiment according to the invention. In this experiment use was made of a catalyst according to the invention which showed both a high activity (expressed as g $C_1^+$/g cobalt/h) and a high stability (expressed as %v loss of CO conversion/100 h). Experiments 6-12 and 14 fall outside the scope of the invention. As is seen from the results of Experiments 8, 10, 12 and 14, in Experiments 6-12 and 14 use was made of catalysts having both too low activity and too low stability.

In Experiments 15-18 a $H_2/CO$ molar ratio of 2 was contacted with Catalysts 14-17 at a temperature of 220° C., a pressure of 30 bar and at various space velocities. The results of these experiments are given in Table V.

Of the experiments mentioned in Table V Experiments 16 and 17 are experiments according to the invention. In these experiments use was made of catalysts according to the invention having both a high activity (expressed as g $C_1^+$/g cobalt/h) and a high stability (expressed as %v loss of CO conversion/1000 h). Experiments 15 and 18 fall outside the scope of the invention. In these experiments use was made of catalysts having both too low activity and too low stability.

Catalytic hydrotreatment

An Experiment 20 was carried out in which at a temperature of 345° C., a pressure of 130 bar, a space velocity of 1.25 l/l/h and a hydrogen/oil ratio of 2000N l/l the $C_5^+$ fraction of the product obtained according to Experiment 13 was passed, together with a hydrogen, through a 50-ml reactor containing a fixed catalyst bed. The catalyst was a $Pt/SiO_2$—$Al_2O_3$ catalyst containing 0.82 pbw platinum per 100 pbw carrier, the carrier consisting 14.6%w of alumina and 85.4%w of silica. The results of Experiment 20 are given in Table VI.

From the results mentioned in Table VI it is seen that when a catalytic hydrotreatment is applied to a product prepared according to the invention, there is conversion of a considerable part of the 400° C.+ fraction (a fall from 37 to 13%w), formation of a considerable quantity of 150°-360° C. fraction (a rise from 43 to 63%w), while only a very minor 150° C.− fraction is formed (a rise from 13 to 17%w).

TABLE I

| Catalyst No. | 1 | 2 | 3 | 4 | 5 | 6 | 7 | 8 | 9 | 10 | 11 | 12 | 13 | 22 |
|---|---|---|---|---|---|---|---|---|---|---|---|---|---|---|
| Co load, pbw/100 pbw $SiO_2$ | 25 | 25 | 10 | 6 | 10 | 25 | 25 | 25 | 25 | 50 | 25 | 25 | 20 | 25 |
| Zr load, pbw/100 pbw $SiO_2$ | 18 | 18 | 18 | 18 | 18 | 1.8 | 0.9 | 0.9 | 0.9 | 1.8 | 1.5 | 2.0 | 10 | 16* |
| L, mg/ml | 105 | 97 | 35 | 24 | 40 | 107 | 103 | 121 | 98 | 190 | 100 | 102 | 76 | 108 |
| S, $m^2$/ml | 28 | 100 | 90 | 104 | 30 | 30 | 31 | 17 | 96 | 43 | 46 | 100 | 84 | 117 |

TABLE I-continued

| Catalyst No. | 1 | 2 | 3 | 4 | 5 | 6 | 7 | 8 | 9 | 10 | 11 | 12 | 13 | 22 |
|---|---|---|---|---|---|---|---|---|---|---|---|---|---|---|
| L/S, mg/m² | 3.75 | 0.97 | 0.39 | 0.23 | 1.33 | 3.57 | 3.32 | 7.12 | 1.02 | 4.42 | 2.27 | 1.02 | 0.90 | 0.92 |

*titanium

TABLE II

| Catalyst No. | 14 | 15 | 16 | 17 | 18 | 19 | 20 | 21 |
|---|---|---|---|---|---|---|---|---|
| Co load, pbw/100 pbw SiO₂ | 25 | 25 | 20 | 10 | 25 | 25 | 25 | 20 |
| Zr load, pbw/100 pbw SiO₂ | 0.9 | 0.9 | 0.8 | 0.4 | 1.5 | 1.8 | 18 | 10 |
| L, mg/ml | 130 | 110 | 84 | 38 | 120 | 126 | 115 | 92 |
| S, m²/ml | 15 | 25 | 68 | 85 | 41 | 22 | 88 | 71 |
| L/S, mg/m² | 8.7 | 4.4 | 1.24 | 0.45 | 2.9 | 5.7 | 1.31 | 1.30 |

TABLE III

| Experiment No. | 1 | 2 | 3 | 4 | 5 | 19 |
|---|---|---|---|---|---|---|
| Catalyst No. | 1 | 2 | 3 | 4 | 5 | 22 |
| Space velocity, Nl gas/l cat/h | 1500 | 2000 | 600 | 300 | 800 | 1500 |
| Initial CO conversion, % v | 85 | 75 | 77 | 66 | 72 | 79 |
| C₁⁺ production, g/l cat/h | 265 | 312 | 96 | 41 | 120 | 246 |
| C₁⁺ production, g/g cobalt/h | 2.5 | 3.2 | 2.7 | 1.7 | 3.0 | 2.3 |
| Loss of CO conversion, % v/100 h | 15 | 7 | 9 | 14 | 7 | 7 |

TABLE IV

| Experiment No. | 6 | 7 | 8 | 9 | 10 | 11 | 12 | 13 | 14 |
|---|---|---|---|---|---|---|---|---|---|
| Catalyst No. | 6 | 6 | 6 | 7 | 7 | 8 | 8 | 9 | 10 |
| Temperature, °C. | 250 | 205 | 220 | 205 | 220 | 220 | 220 | 220 | 220 |
| Pressure, bar | 30 | 20 | 20 | 20 | 20 | 30 | 20 | 20 | 20 |
| Space velocity, Nl gas/l cat/h | 2000 | 2000 | 700 | 2000 | 700 | 600 | 600 | 1000 | 1500 |
| H₂/CO molar ratio of feed | 1 | 3 | 2 | 3 | 2 | 2 | 2 | 2 | 2 |
| Initial CO conversion, % v | | 38 | 73 | 43 | 83 | 85 | 78 | 85 | 79 |
| C₁⁺ production, g/l cat/h | 280 | | 106 | | 121 | | 97 | 176 | 245 |
| C₁⁺ production, g/g cobalt/h | | | 0.99 | | 1.2 | | 0.80 | 1.8 | 1.3 |
| Loss of CO conversion, % v/100 h | | | 14 | | 13 | 24 | 21 | 9 | 15 |

TABLE V

| Experiment No. | 15 | 16 | 17 | 18 |
|---|---|---|---|---|
| Catalyst No. | 14 | 15 | 16 | 17 |
| Space velocity, Nl gas/l cat/h | 600 | 800 | 700 | 300 |
| Initial CO conversion, % v | 80 | 72 | 76 | 65 |
| C₁⁺ production, g/l cat/h | 100 | 120 | 110 | 40 |
| C₁⁺ production, g/g cobalt/h | 0.77 | 1.1 | 1.3 | 1.0 |
| Loss of CO conversion, % v/1000 h | 54 | 39 | 45 | 68 |

TABLE VI

| Composition % w | C₁⁺ product of Experiment 13 | C₅⁺ fraction of the C₁⁺ product of Experiment 13 | C₁⁺ product after catalytic hydro-treatment |
|---|---|---|---|
| C₄⁻ | 17 | — | 1 |
| C₅-150° C. | 11 | 13 | 16 |
| 150-250° C. | 17 | 21 | 27 |
| 250-360° C. | 18 | 22 | 36 |
| 360-400° C. | 6 | 7 | 7 |
| 400° C.⁺ | 31 | 37 | 13 |

What is claimed is:

1. A process for the preparation of a catalyst by kneading and/or impregnation, which catalyst comprises 3-60 pbw cobalt and 0.1-100 pbw of at least one other metal chosen from zirconium, titanium or chromium per 100 pbw of a carrier chosen from silica, alumina or silica-alumina, characterized in that said catalyst has such L and S as to satisfy the relation $(3+4R) > (L/S) > (0.3+0.4R)$, wherein L = the total quantity of cobalt present on the catalyst, expressed as mg Co/ml catalyst;

S = the surface area of the catalyst, expressed as m²/ml catalyst; and

R = the weight ratio of the quantity of cobalt deposited on the catalyst by kneading to the total quantity of cobalt present on the catalyst or R=0 when catalyst prepared by impregnation.

2. The process of claim 1, characterized in that both during impregnation and during kneading the carrier material is contacted with a solution of the metal compound involved.

3. The process of claim 1, characterized in that the cobalt is deposited from a solution of an inorganic cobalt compound in water.

4. The process of claim 1, characterized in that the other metal is deposited from a solution of an organic metal compound in an organic solvent or mixture of organic solvent or mixture of organic solvents.

5. The process of claim 4, characterized in that the organic solvent consists at least partly of a β-diketone or β-keto-ester.

6. The process of claim 5, characterized in that the solution comprises more than 0.5 gram molecule of a β-diketone or β-keto-ester per gram atom of the other metal.

7. The process of claim 1, characterized in that during impregnation a quantity of liquid is used, the volume of which corresponds substantially with the pore volume of the carrier to be impregnated.

8. The process of claim 1, characterized in that during kneading a quantity of liquid is used, the volume of which corresponds substantially with 110-190% of the pore volume of the carrier.

9. The process of claim 1, characterized in that the composition obtained is calcined after each impregnation or kneading step.

10. The process of claim 1, characterized in that first the cobalt is deposited in one or more steps by impregnation, and subsequently the other metal is deposited in one or more steps, also by impregnation.

11. The process of claim 1, characterized in that first the other metal is deposited in one or more steps by impregnation, and subsequently cobalt is deposited in one or more steps, also by impregnation.

12. The process of claim 1, characterized in that first cobalt is deposited in one or more steps by kneading, and subsequently the other metal is deposited in one or more steps by impregnation.

13. The process of claim 1, characterized in that a catalyst is prepared which comprises 15-50 pbw cobalt per 100 pbw carrier.

14. The process of claim 1, characterized in that first cobalt is deposited, and subsequently the other metal, and that a catalyst is prepared which comprises 0.1-5 pbw of the other metal per 100 pbw carrier.

15. The process of claim 1, characterized in that first the other metal is deposited and subsequently the cobalt, and that a catalyst is prepared which comprises 5-40 pbw of the other metal per 100 pbw carrier.

16. The process of claim 1, characterized in that the other metal used is zirconium.

17. The process of claim 1, characterized in that the carrier used is silica.

* * * * *